(12) United States Patent
Nelen

(10) Patent No.: US 6,359,277 B1
(45) Date of Patent: Mar. 19, 2002

(54) METHOD AND APPARATUS FOR DETECTING COATINGS

(75) Inventor: Lucien Johannes Nelen, Worcester (GB)

(73) Assignee: Sencon Europe Limited (GB)

( * ) Notice: Subject to any disclaimer, the term of this patent is extended or adjusted under 35 U.S.C. 154(b) by 0 days.

(21) Appl. No.: 09/558,268

(22) Filed: Apr. 25, 2000

(30) Foreign Application Priority Data

May 1, 1999 (GB) .............................. 9910006

(51) Int. Cl.$^7$ .................. G01J 5/02; G01J 5/00
(52) U.S. Cl. ................ 250/341.1; 250/338.1; 250/340
(58) Field of Search .............. 250/341.8, 340, 250/338.1, 336.1

(56) References Cited

U.S. PATENT DOCUMENTS

| | | | |
|---|---|---|---|
| 5,144,151 A | * 9/1992 | Thorne et al. | 250/341.1 |
| 5,191,803 A | 3/1993 | Gamache | |
| 5,568,251 A | 10/1996 | Davies et al. | |

FOREIGN PATENT DOCUMENTS

| | | |
|---|---|---|
| EP | 0071316 | 2/1983 |
| EP | 0119630 | 9/1984 |
| EP | 0300734 | 1/1989 |
| GB | 2227091 | 7/1990 |
| WO | WO8700629 | 1/1987 |

OTHER PUBLICATIONS

Search Report Jul. 16, 1999.

* cited by examiner

Primary Examiner—Hung Xuan Dang
(74) Attorney, Agent, or Firm—Ira S. Dorman (57) ABSTRACT

A coating is detected on a substantially planar object (9), such as a sheet, which is moving in a predetermined direction. The object has a coating (30) on at least a part of its planar surface, which coating is at least partially transparent to visible radiation. An emitter (33) is adapted to emit a beam of substantially non-visible electromagnetic radiation having a predetermined wavelength range towards the object (9). A scanner (36) is adapted to scan the beam of electromagnetic radiation in a direction that has at least a component transverse to the predetermined direction. A sensor (34) detects radiation in the predetermined wavelength range which is reflected in a specular manner by the object (9). The presence and/or absence of a coating (30) on the object is determined on the basis of the magnitude of specularly reflected radiation.

33 Claims, 7 Drawing Sheets

METHOD AND APPARATUS FOR DETECTING COATINGS

This invention relates to a method and an apparatus for detecting coatings and has particular application, for example, to plain margin detectors for the detection of an acceptable plain margin that is to be joined in can production.

BACKGROUND TO THE INVENTION

A discussion of a typical manufacturing process for three-part cans, and a discussion of at least some of the problems encountered in welding a blank into a tube associated with a failure to obtain a good plain margin of unlacquered sheet, is given later with reference to FIGS. 1 to 4 of the accompanying drawings. The reader is directed to read this text now in order to put the invention into context.

OBJECT OF THE INVENTION

It is an object of the invention to provide an apparatus and a method for detecting a coating whether that coating is wet or dry.

SUMMARY OF THE INVENTION

According to one aspect of the present invention there is provided an apparatus for detecting a coating on a substantially planar object which is moving in a predetermined direction relative to the apparatus, the object having a coating on at least a part of the planar surface thereof, which coating is at least partially transparent to visible radiation, the apparatus comprising:

an emitter adapted to emit a beam of substantially non-visible electromagnetic radiation having a predetermined wavelength range towards the object;

scanning means adapted to scan the beam of electromagnetic radiation in a direction that has at least a component transverse to the predetermined direction;

a sensor for detecting radiation in the predetermined wavelength range which is reflected in a specular manner by the object; and means for determining the presence and/or absence of a coating on the object on the basis of the magnitude of specularly reflected radiation.

According to another aspect of the present invention there is provided a method of detecting a coating on a planar object which is moving in a predetermined direction, the object having a coating on at least a part of the planar surface thereof, which coating is at least partially transparent to visible radiation, the method comprising the steps of:

emitting a beam of substantially non-visible electromagnetic radiation having a predetermined wavelength range towards the object;

scanning the beam of electromagnetic radiation in a direction that has at least a component transverse to the predetermined direction;

sensing radiation in the predetermined wavelength range which is reflected in a specular manner by the object; and determining the presence and/or absence of a coating on the object on the basis of the magnitude of specularly reflected radiation.

When embodied in a plain margin detector, this enables us to check sheets of lacquered (coated) sheet material (e.g. steel) whilst the lacquer is wet or dry, preferably when the lacquer is wet immediately after lacquering.

Thus, in practice the radiation is differentially absorbed/reflected between an uncoated region and a coated region, and the sensor is adapted in use to detect that radiation.

Preferably the sensor is an optical sensor.

Preferably the radiation is absorbed by the coating more than it is by the substrate material of the object.

Preferably the radiation is emitted at a wavelength that is at, or near enough to, the absorption wavelength of a component of the lacquer, any solvent used to apply the lacquer, or the substrate material, so that it is in use absorbed. For example, the radiation wavelength may be in the near infrared or in the ultraviolet region of the spectrum.

When in the near infrared region, the radiation wavelength may be substantially at the absorption wavelength of the C—H bond (on at least one of its absorption wavelengths). Most lacquers, e.g. phenolic lacquers, epoxy lacquers and vinyl lacquers, have C—H bonds. Steel, of course, does not (nor does any metal).

Looking for a C—H bond is a very good way of detecting whether or not there is a coating on an object, for example of detecting a plain margin and checking that the plain margin has no lacquer thereon. Conversely, it is also a good way of detecting uncoated regions in a coated object. The precise absorption wavelength of a C—H bond depends upon its environment—what structural groups are next to the C—H bond in its molecule and even to some extent what other chemicals (e.g. solvents) are present. I have found that 3.3 $\mu$m is a suitable wavelength for all, or at least a significant number of, common coating lacquers used in the production of cans. When employing near infrared radiation I can therefore use radiation of 3.3 $\mu$m, plus or minus 0.1, or 0.2, or 0.3 $\mu$m. Nevertheless, I have also found that 2.3 $\mu$m (plus or minus 0.1, or 0.2, or 0.3 $\mu$m) also works well in the near infrared region of the electromagnetic spectrum.

Alternatively, many lacquers are water-based and water absorbs strongly at 1.96 $\mu$m and this represents another very good way of detecting whether or not there is a coating on an object, for example of detecting a plain margin and checking that the plain margin has no lacquer thereon. Alternatively, it is a good way of detecting uncoated regions in a coated object. Thus, I can also employ near infrared radiation of 1.96 $\mu$m, plus or minus 0.1, or 0.2, or 0.3 $\mu$m.

Alternatively, I have found that most coating materials absorb electromagnetic radiation in the region of 200 to 360 nm, while metals do not. Thus, looking for absorption or reflection in the region of 200 to 360 nm, preferably about 254 nm because monochromatic light eliminates aberrations, is another very good way of detecting whether or not there is a coating on an object, once again for example, of detecting a plain margin and checking that the plain margin has no coating thereon. Conversely, it is also a good way of detecting uncoated regions in a coated object. We have found that the range of 200 to 360 nm is a suitable wavelength for all, or a significant number of, common coating lacquers used in the production of cans. Depending on the wavelength of radiation required, the emitter could comprise a halogen (for infrared radiation) or a low pressure mercury (for ultraviolet radiation) light source.

Alternatively, and in particular for detecting infrared radiation, I may use a solid state emitter such as a laser or a light-emitting diode (LED). A laser or an LED can have a small emitting surface area (e.g. about 1 mm$^2$), which is easier to focus to a small point than is light from a large surface area. I prefer to chop the emitted and/or detected signal to amplify a narrow frequency band. This reduces background noise. An LED can be chopped electronically rather than mechanically. I prefer to chop electronically. The chopping frequency is preferably more than 50 kHz, and most preferably about 100 kHz or more. It is possible to chop this fast mechanically, but it is expensive to do so.

It is cheaper and more reliable to switch LEDs on and off electronically in order to chop the emitted signal. LEDs are also quieter than a mechanical chopper. Thus the sensor preferably has emitted signal chopping means, most preferably electronic chopping of an LED.

The scanning means may comprise a mechanical scanner, or an electronic scanner. An electronic scanner may comprise, for example an emitter and/or a sensor in the form of a linear array of emitters and/or sensors. A linear array of sensors may comprise, for example, a linear CCD device.

Preferably the scanning means is adapted to scan a beam of radiation back and forth (reciprocally), for example along a line. Preferably in use the object, such as a sheet of uncut blanks, and the detector experience relative movement during a scanning operation. Preferably the object is moved relative to the scanning means, but alternatively the scanning means may move relative to the object.

The transverse component of movement is preferably substantially perpendicular to the predetermined direction of movement of the object.

The scanning means preferably scans back and forth along a line at a frequency of at least 1 kHz, preferably at least 5 kHz, and most preferably at 10 kHz or above.

Preferably the scanning means and the chopping means are adapted to pulse the radiation onto object at intervals of about 3 mm or less, or about 2 mm or less, or about 1 mm or less, or about 0.5 mm or less, or about 0.3 mm or less.

Preferably the detector has radiation gathering means (e.g. a mirror), and focussing means (e.g. a mirror or a lens) to focus the specularly reflected radiation onto a radiation-sensitive transducer.

The scanner may scan electronically. It may have a plurality of emitters which emit radiation which in use falls on different regions of the object. The emitters may be operated sequentially.

Particularly, but not exclusively, for ultraviolet radiation, the radiation may be emitted in a narrow divergent beam which is reflected by one of the coated or uncoated surface (usually the uncoated surface) and absorbed by the other. The diverging beam is focussed onto a detector by a mirror or a lens. The detector may be an array of detectors which may be scanned or may be a single detector.

The means for determining the presence and/or absence of a coating on the basis of any reflected radiation may comprise signal processing means adapted to process the signals detected by the sensor. The processing means may produce a signal indicative of a fault if it concludes there is a fault in the coating on the object. The signal processing means has reference data with which it compares a received signal sequence from the sensor to determine if there is a fault in the coating or not. The reference data is updated automatically by the signal processing means.

The apparatus may be incorporated into a can producing line. Preferably the line has line control means which controls the operation of the line. The detector preferably provides signals to the line control means which uses the signals to control the operation of a coating station of the line. If a fault signal is received from the detector (which may itself have an internal protocol for avoiding false fault signals being sent to the line control means) the line control means may be arranged to stop the coating station and/or cause an alarm to be activated.

The prior art and embodiments of the invention will now be described with reference to the accompanying drawings in which.

BRIEF DESCRIPTION OF THE DRAWINGS

DESCRIPTION OF PRIOR ART

Figure 1:
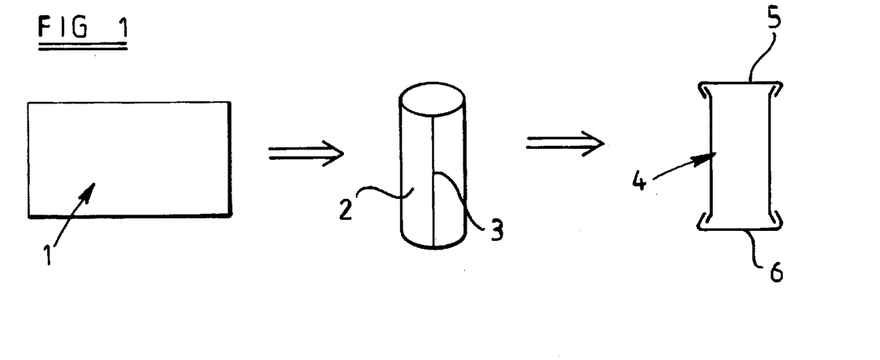
FIG. 1 illustrates schematically the formation of a three-part can from a can blank.

FIG. 1 shows a blank, referenced 1, which is formed into a tubular body, referenced 2, and then welded along axial weld line 3 to form a main body portion of a can, referenced 4. A top 5 and a bottom 6 are attached to the body (e.g. by crimping). This is how standard three-part cans are made.

Figure 2:
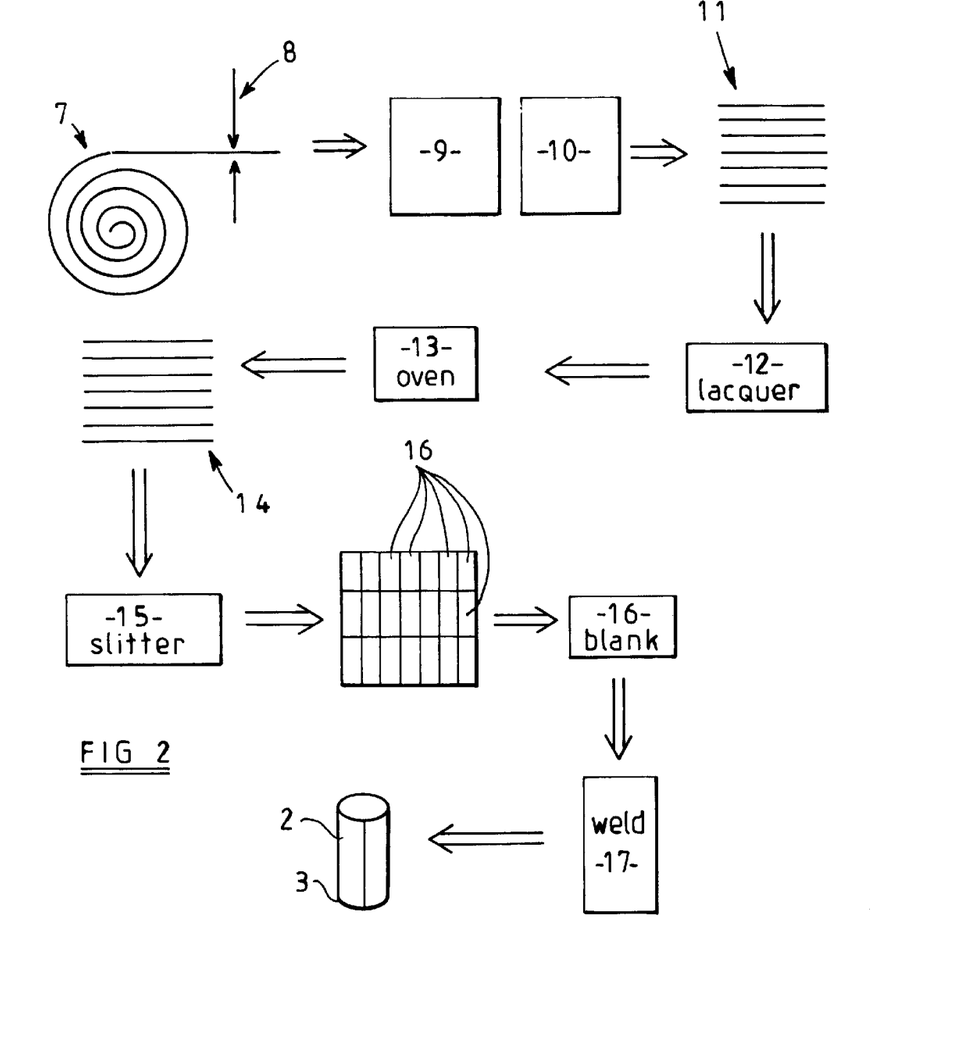
FIG. 2 illustrates schematically part of the production line for a can.

FIG. 2 shows schematically parts of the assembly process/line. A large roll 7 of metal sheet, such as steel, is fed through a cutting station 8 (which typically comprises reciprocating shears) to cut the strip of steel into separate sheets (two of which are referenced 9 and 10). The sheets, which are typically roughly square and about 1 m², are then stacked (shown at 11) and fed in turn to a lacquering station 12 where lacquer is applied to the sheet metal. The sheets 9, 10 are then dried in an oven for about 20 to 30 minutes, and are then stored again in stacks (referenced 14). Some time after any particular sheet 9 enters the store of dried lacquered sheets, typically a day or two later, it is taken and passed to a slitter 15 (can producing plants typically keep a large store of ready lacquered sheets) which cuts the sheet 9 into separate blanks 16. The blanks 16 enter a welding station where they are rolled and welded to form the tubular can body 2.

Figure 3:
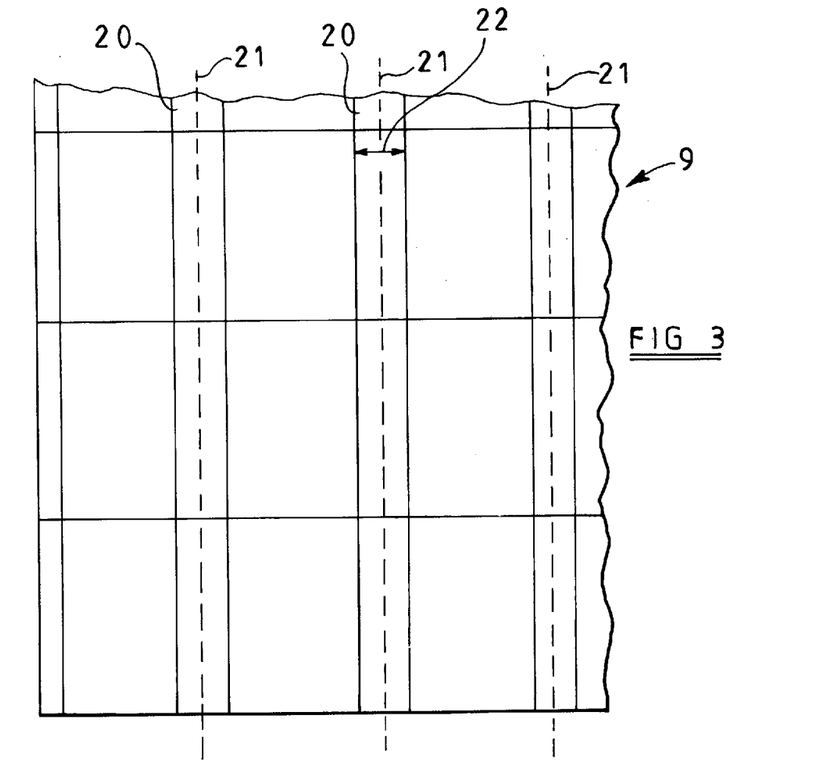
FIG. 3 illustrates schematically a sheet of metal lacquered to leave unlacquered margins where the sheet is to be welded, following cutting.

The welding of the axial seam of the can body is done electrically by passing a large current through slightly overlapped (e.g. 0.3 mm) axially extending edge portions of the folded blank. The lacquer used to coat the sheet metal is a good electrical insulator and so the regions of the blank to be welded to each other should have no lacquer overlying them. When the sheets 9 are lacquered at the lacquering station, the sheets are not fully covered but instead lacquer-free strips, called plain margins, are left between what will be separate blanks so that the electric current can flow during welding. The slitter 15 cuts the sheets 9 down the middle of the plain margins to leave an unlacquered strip to each axial side of the blanks. This is schematically shown in FIG. 3. The plain margins are referenced 20, and the cut lines where the slitter will cut in the plain margins are referenced 21. The width of a plain margin between adjacent blanks, shown at 22, is typically about 6 mm.

If the lacquering machine is not working properly, or if the sheets 9 are misaligned or not registered properly with the lacquering machine, there can be faults which can make welding problematic. If there is lacquer in the weld zone during welding there can be large sparks, and the welding machine can be damaged. Most welding machines have weld monitoring control systems to shut them down if there is a power surge or other weld problem, but when blanks are being welded at high speed the control systems can be too slow to prevent damage. Also a can may be made having a poor weld which might be dangerous at a later date. A typical welding station has a cylindrical weld support to go inside the tubular folded can blank and to conduct the welding current. These welding components are very expensive, are typically mercury filled, and have a groove in which a copper wire is received. This copper wire is what is actually under the weld line. The copper wire is continually replaced and is strung over a series of wire tensioners and drive mechanisms (if it were not a replaceable/replaced wire receiving the weld current the mercury filled weld support cylinder would itself wear very quickly). If there is a high resistance in the weld the copper wire can break. The wire then needs to be re-threaded into the groove in the weld support cylinder, and over the tensioning and drive components. This can shut down the weld station for 20 to 30 minutes, which is undesirable since it causes a bottleneck in the production process.

Figures 4A, 4B:
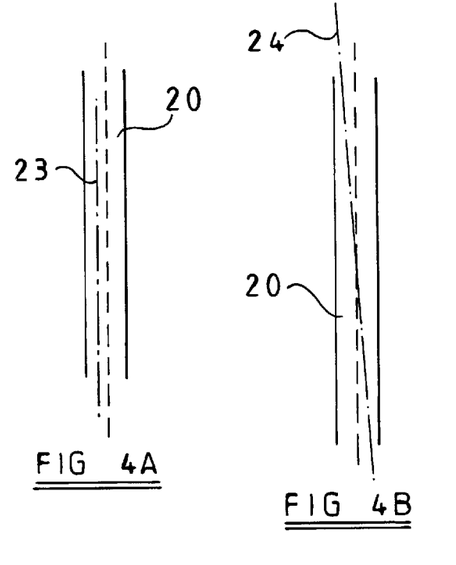
FIGS. 4A to 4C show problems that can occur during lacquering.

FIG. 4A shows a lateral translation of the sheet 9 relative to where it should be when the lacquer is applied and shows that in the case of translation of the sheet the slitter will not cut in the centre of the plain margin 20, but off-centre along line 23. This means that the blanks will have one side margin that is too narrow and another that is too broad. The narrow margin may mean that during welding the lacquer interferes with the formation of a proper weld, with the possibility of shutting down the welding station.

FIG. 4B shows a problem with the orientation of the sheet 9 relative to the lacquering machine. The sheet has been fed in rotated, or skewed. When the slitter cuts along line 24, the margin to a side of a cut blank will taper axially, or even not be present on some blanks, and this can cause the weld problems, and downtime, discussed hereinabove.

Figure 4C:
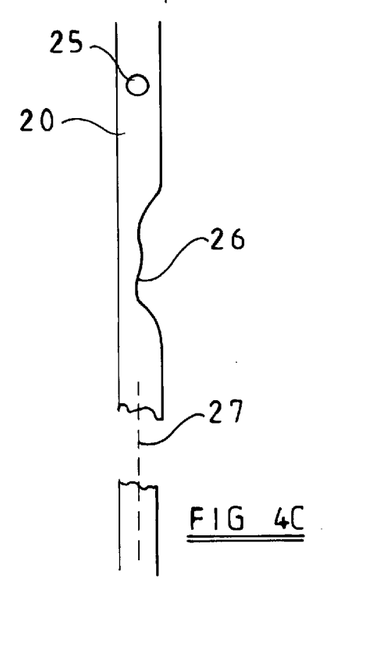

FIG. 4C shows a plain margin 20 with a spot 25 of lacquer in the margin. The figure also shows a projecting edge portion 26 of lacquer that has protruded into the plain margin. The figure further shows a bridge of lacquer 26 that extends across the plain margin. All three of these defects can cause weld problems.

Because of the problems of lacquer being present in the plain margins, it is known to have a plain margin detector in the production line. A plain margin detector is needed because the lacquers used are substantially transparent which renders visual inspection of the laquer difficult or impossible. A plain margin detector is used between the store 14 and the slitter 15, or between the oven 13 and the store 14. Known plain margin detectors have a conductive fibre brush or conductive wheel that is biased towards the sheet 9 and is moved relative to the sheet (or the sheet moved relative to the conductor) along the plain margins. A low current is passed to the conductor and is monitored. When the conductor passes over dried lacquer there is a drop in current, indicating lacquer coverage. Such plain margin detectors work well.

DESCRIPTION OF PREFERRED EMBODIMENTS

However, I have appreciated that known plain margin detectors do have some problems. Because known detectors can be used only after the lacquer has dried (otherwise they can simply draw wet lacquer over the plain margins they are supposed to be monitoring, thus ruining the plain margins) there will be at the very least 20 to 30 minutes worth of lacquered sheets (perhaps over $1600 worth of steel) in the oven waiting to dry when any problem is detected. If there is a fault with the lacquering process many lacquered sheets may have to be thrown away. My plain margin detector allows me to check a sheet when the lacquer is wet, which has not previously been possible. This gives me much faster feedback and enables me to avoid having a large quantity of wet lacquered sheets waiting around before I detect a problem on a dried lacquer sheet. This can save thousands of dollars for each lacquering fault that occurs by not wasting so much steel.

Figure 5A:
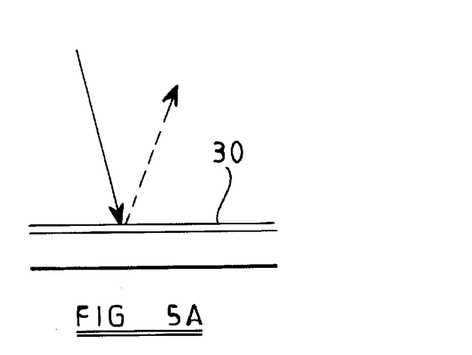
FIGS. 5A and 5B show. schematically the absorption and reflection, respectively, of light from a lacquered surface and an unlacquered surface respectively.
Figure 5B:
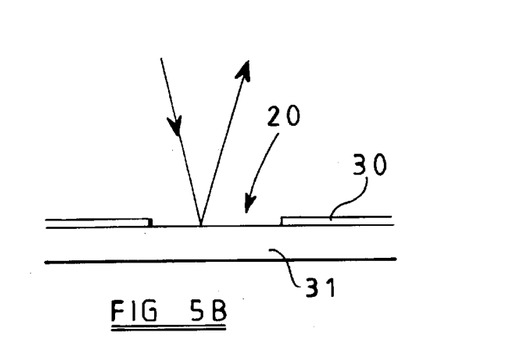

FIGS. 5A and 5B schematically show the principle of my detector: radiation of a particular wavelength is absorbed by the lacquer 30, but not by the bare metal 31 of the plain margin 20. The difference in a signal generated from reflected radiation is detected at the boundary between the coating and the plain margin.

Figure 8A:
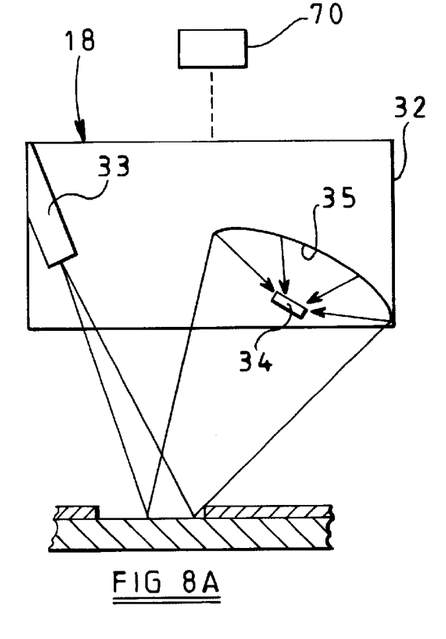
FIGS. 8A and 8B show schematically further details of the detector of FIG. 6A.

My plain margin detector unit, referenced 18, is schematically illustrated in FIG. 8A and comprises a housing 32 which holds an emitter 33 of suitable electromagnetic radiation which is emitted in a narrow divergent beam, a sensor 34 for detecting reflected radiation originating from the emitter, and a focussing mirror 35 adapted to focus specularly reflected radiation onto the sensor 34. The electromagnetic radiation may be of any suitable substantially non-visible wavelength, such as ultraviolet radiation having a wavelength, for example, in the range of about 200 nm to about 360 nm, preferably about 254 nm, or infra-red radiation having a wavelength, for example, of about 3.3 $\mu$m or about 2.3 $\mu$m or about 1.96/m. The sensor 34 is, in use, generally above the plain margin, and the emitter 33 is offset and angled to direct its radiation onto the plain margin.

Figure 8B:
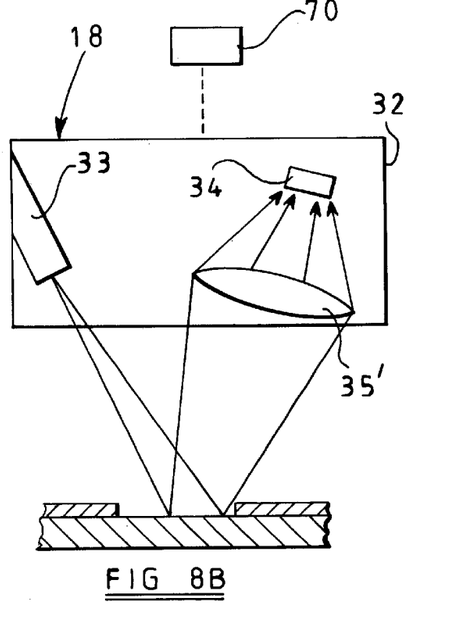

As an alternative to a focussing mirror, a lens 35' may be provided as shown in FIG. 8B.

For example, if desired, I could add a component to the at least partially transparent lacquer/solvent which is easily detected by radiation of a particular wavelength and then use an emitter/detector sensitive to that wavelength.

Figure 11:
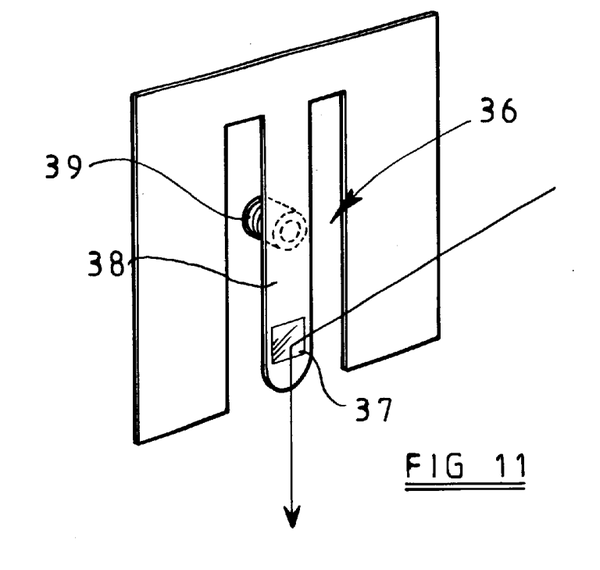
FIG. 11 shows schematically details of the emitter part of the detector of FIG. 6A.

In practice the emitter 33 may direct its radiation onto scanning means 36 (not shown in FIG. 8 but shown in FIG. 11). The scanning means, where provided, is also mounted in the housing 32 and comprises a mirror 37 mounted on a movable support (finger in this example) 38. An electrically powered motive means 39 (e.g. piezoelectric, solenoid, etc.) moves the support in response to variations in current.

Figure 6A:
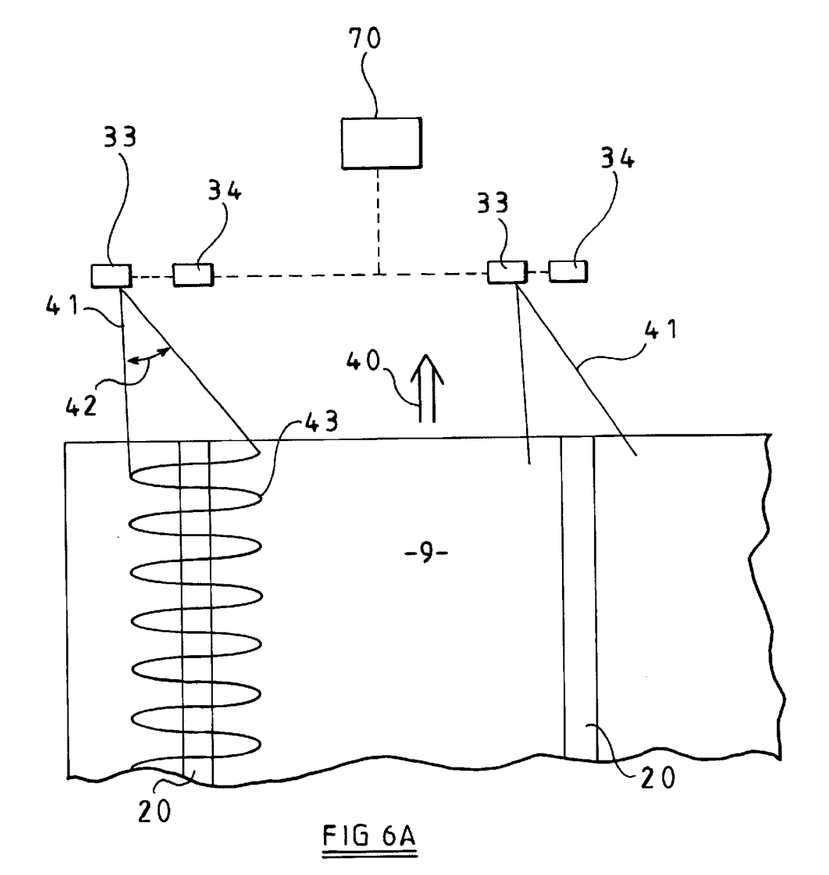
FIGS. 6A and 6B illustrate schematically two similar embodiments of an apparatus in accordance with the present invention in the form of a plain margin detector.

The effect to be achieved is shown in FIG. 6A. The plate 9, which is substantially planar, is moved in a predetermined direction relative to a plurality of detector units 18, i.e., in the direction of arrow 40. The beams 41 from the emitters 33 are scanned to and fro through an arc 42 (using the scanning means of FIG. 11). The combination of these movements produces a sinusoidal trace, referenced 43. The beams therefore scan across the plain margins 20. Rather than in fact being continuous beams, the beams 41 are chopped (or pulsed). This reduces background noise effects when the detected signal is amplified. The emitters are LEDs or lasers which emit radiation at the desired frequency. The beams are chopped electronically by pulsing the emitters 33 at about 100 kHz.

The finger 38 is oscillated at about 10 kHz, and there are thus about 10 samples per scan. I may prefer to take more samples, e.g. 20, 30, 40 or 50 or more per scan.

Figure 6B:
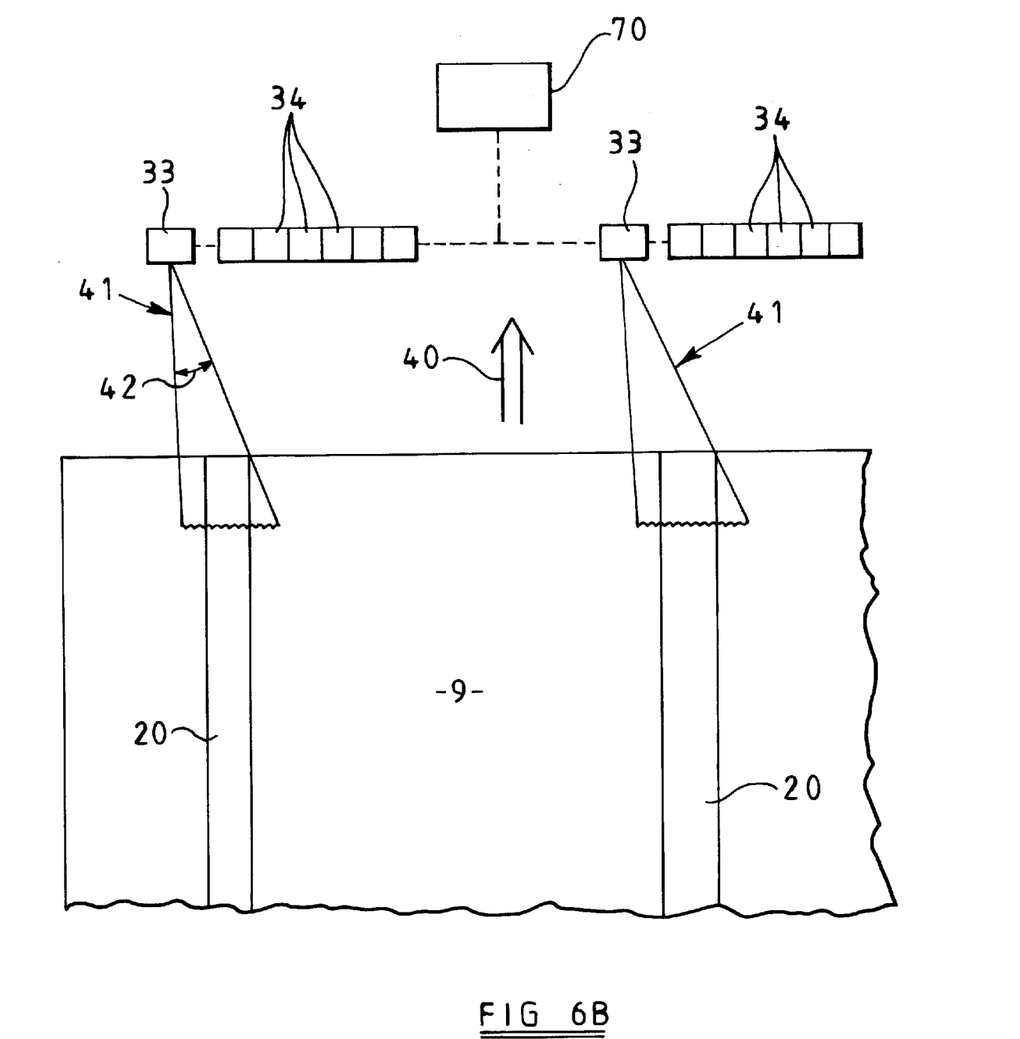

As an alternative to a single sensor 34 and scanning means 36, I can use an emitter 33 which emits radiation 41 in a fantail configuration having an arc 42 and a plurality of sensors 34, for example in the form of a linear array as illustrated in FIG. 6B.

I prefer to have the plain margins about 5 to 6 mm wide, and to have the scan go 3 mm or so to each side of the margins giving a scan length of about 12 mm, and preferably not more than about 20 mm.

I scan a sheet whilst the lacquer is wet, preferably immediately after the lacquer has been applied. Alternatively, or additionally, I can, of course, scan dry lacquer. If I scan wet lacquer I may look for absorption of radiation caused by solvent. This typically has a C—H bond which absorbs strongly in the region of 3.3 $\mu$m and/or incorporates water which absorbs strongly at about 1.96 $\mu$m. Alternatively, I can look for other absorption or reflective properties of the coating material and I have found that most coating materials absorb strongly in the range from 200 to 360 nm.

Figure 9:
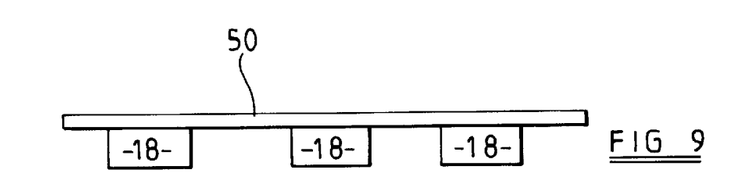
FIG. 9 shows schematically a plurality of detectors mounted on a support arm to enable a plurality of margins to be checked simultaneously.

Every plain margin has its own detector unit in my preferred system. FIG. 9 shows an arm 50 which in use extends across a sheet 9, possibly at the exit from the lacquering station. The arm 50 carries a plurality of detector units 18.

Figure 10:
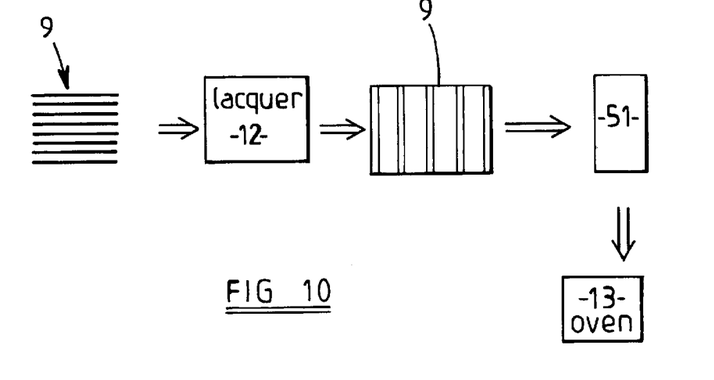
FIG. 10 schematically shows a part of the production system for can blanks using the present invention.

FIG. 10 shows a stack of sheets 9 being fed to a lacquering station 12 and then proceeding to an optical plain margin detector 51 whilst they are still wet, and then going to an oven 13.

Figure 7A:
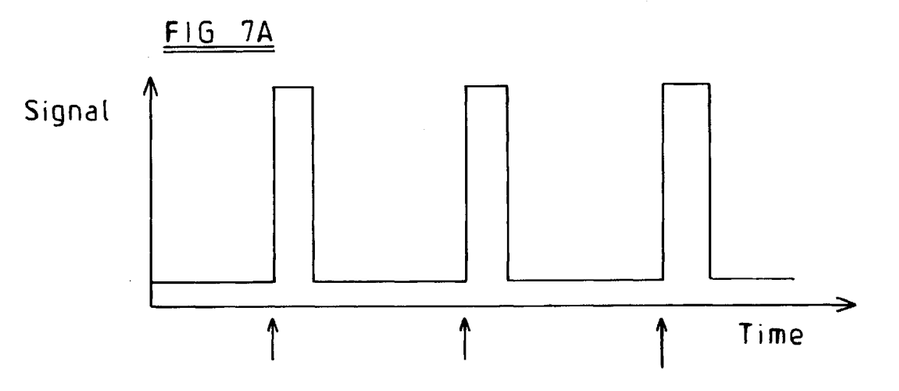
FIGS. 7A to 7D show schematically the received signal for a good plain margin and a number of faulty margins.

FIGS. 7A to 7D show the signal traces for different problems. FIG. 7A shows the signal for a good plain margin. (It will in fact be a series of discrete points where the emitter beam is chopped. With a chopped beam I aim to have at least three points in any plain margin).

Figure 7B:
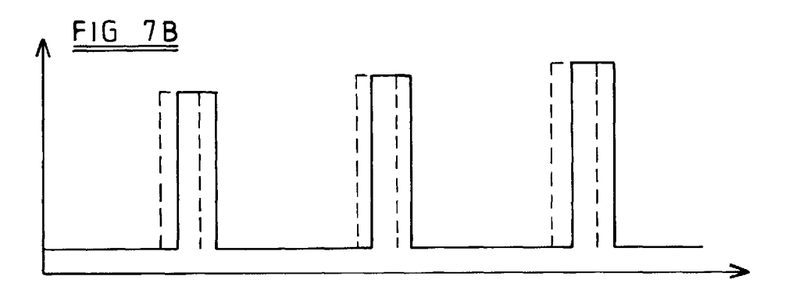

FIG. 7B shows the signal if the sheet is translated relative to the lacquering mechanism. The control processor (not shown) present in the detector unit (or associated with the detector unit, perhaps mounted on the arm 50) knows where, relative to a reference point of the sheet 9 (perhaps a first edge), the first leading edge of the peaks should be (referenced as 52 in FIG. 7A).

If the peaks occur too soon, or too late, in relation to a margin at an edge of the sheet, but are nevertheless the correct distance apart, then this can indicate translation.

Figure 7C:
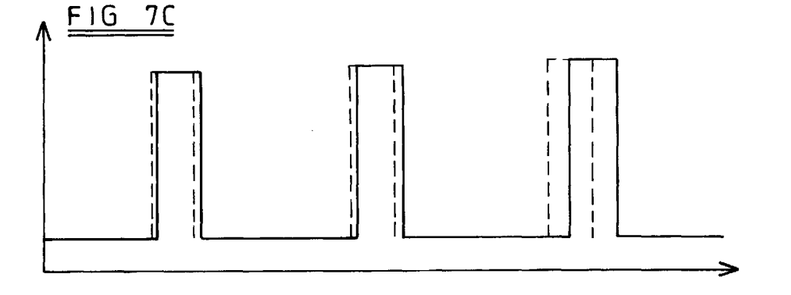

FIG. 7C shows a gradual shifting of the peaks. This can indicate, in relation to a margin at an edge of the sheet, a skewed plate.

Figure 7D:
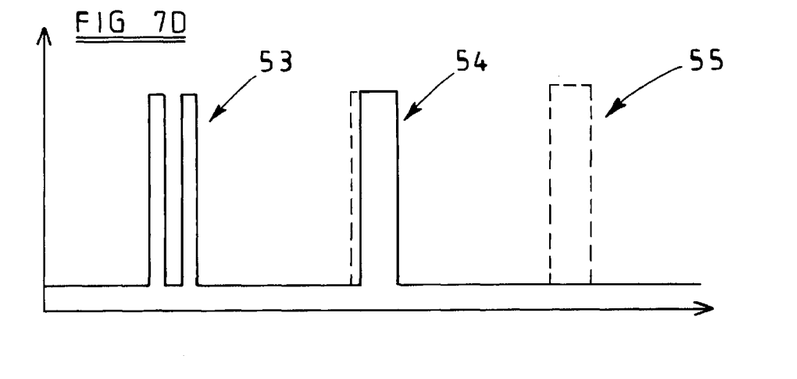

FIG. 7D shows at 53 a double peak, at 54 a narrow peak, and at 55 no peak. These can indicate a spot (such as spot 25), a projection of lacquer (such as projection 26), and a bridge of lacquer (such as bridge 27).

The control means 70 of the detectors may be able to teach itself to recognise different allowable trace patterns (to allow for different sized can blanks being made). It may be able to allow a very gradual drift in signal strength due to drying lacquer, or a slightly different lacquer (or indeed a very different lacquer). The control means will also be able to compensate for intensity variations due to sheet movement. In this respect, the difference in signal strength between coated and uncoated areas is calculated as a ratio rather than as absolute values and a threshold for determining the presence or absence of a coating is calculated for each scan.

Figure 12:
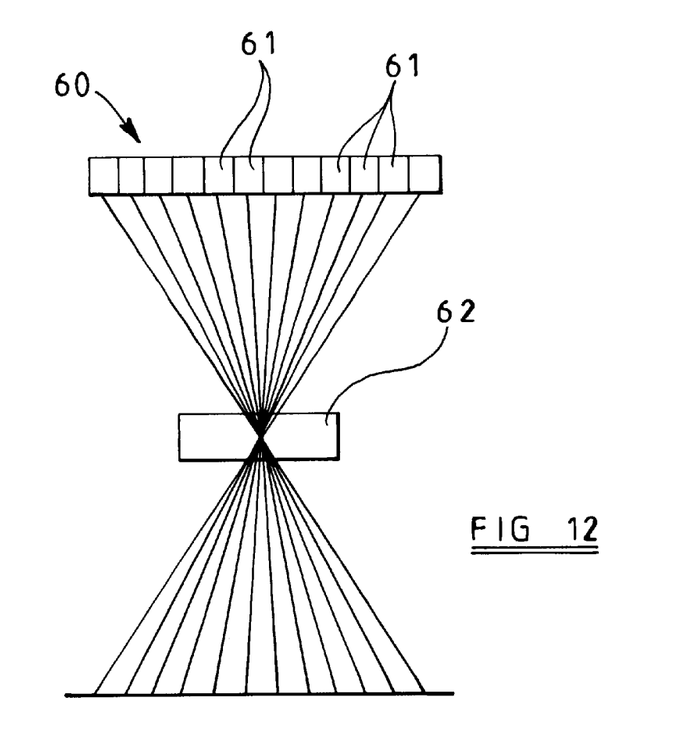
FIG. 12 shows schematically an alternative emitter arrangement for an apparatus according to the present invention, such as a plain margin detector.

FIG. 12 shows an alternative way of scanning the beam of emitted radiation. An array 60 of LEDs 61 is provided. The LEDs direct their radiation in different directions (in this example, but not necessarily) and are activated in sequence so as to cause the row of spot samples to traverse a plain margin.

A lens 62 may be provided to focus the emitted radiation.

It will be appreciated that instead of, or most preferably in addition to, checking the plain margins of a sheet before the sheet is cut into blanks I could check the plain margins of individual cut blanks (or one-blank wide strips of blanks). This would enable us to detect faults with the slitter arrangement.

A detector similar to that for checking the wet lacquer could then be provided for dry sheets after the slitter or on the welder itself (with either a single or a double head). Appropriate feedback to the overall production line could again be provided.

Furthermore, although described with reference to checking plain margins on sheets for making can blanks, the sheets could be used to make anything (not necessarily can blanks). That is, I can check for the presence or absence of a coating in general and could be used, for example, to detect unlacquered, or uncoated, spots on a coated sheet.

I claim:

1. An apparatus for detecting a coating on a substantially planar object which is moving in a predetermined direction relative to the apparatus, the object having a coating on at least a part of the planar surface thereof, which coating is at least partially transparent to visible radiation, the apparatus comprising:
    an emitter adapted to emit a beam of substantially non-visible electromagnetic radiation having a predetermined wavelength range towards the object;
    scanning means adapted to scan the beam of electromagnetic radiation in a direction that has at least a component transverse to the predetermined direction;
    a sensor for detecting radiation in the predetermined wavelength range which is reflected in a specular manner by the object; and
    means for determining the presence and/or absence of a coating on the object on the basis of the magnitude of specularly reflected radiation.

2. An apparatus according to claim 1 and including means for chopping the emitted signal to facilitate amplification of a narrow frequency band.

3. An apparatus according to claim 2, wherein the chopping frequency is more than 50 kHz.

4. An apparatus according to claim 1 and including means for chopping the detected signal to facilitate amplification of a narrow frequency band.

5. An apparatus according to claim 4, wherein the chopping frequency is more than 50 kHz.

6. An apparatus according to claim 1, wherein the scanning means comprises an electronic scanner.

7. An apparatus according to claim 6, wherein the electronic scanner comprises at least one of an emitter and a sensor in the form of a linear array.

8. An apparatus according to claim 7, wherein the linear array comprises a linear CCD device.

9. An apparatus according to claim 6, wherein the scanning means comprises a plurality of emitters which emit radiation which in use falls on different regions of the object.

10. An apparatus according to claim 9, wherein the emitters are operated sequentially.

11. An apparatus according to claim 1, wherein the scanning means is adapted to scan the beam of radiation back and forth.

12. An apparatus according to claim 1, wherein the transverse component is substantially perpendicular to the predetermined direction.

13. An apparatus according to claim 1 and including radiation gathering means.

14. An apparatus according to claim 13, wherein the radiation gathering means includes focussing means to focus the specularly reflected radiation onto the sensor.

15. An apparatus according to claim 1, wherein the means for determining the presence and/or absence of a coating comprises signal processing means adapted to process signals generated by the sensor in response to any specularly reflected radiation.

16. An apparatus according to claim 15, wherein the signal processing means incorporates reference data with which it compares a received signal sequence from the sensor to determine if there is a fault in the coating or not.

17. An apparatus according to claim 16, wherein the reference data is updated automatically by the signal processing means.

18. A method of detecting a coating on a planar object which is moving in a predetermined direction, the object having a coating on at least a part of the planar surface thereof, which coating is at least partially transparent to visible radiation, the method comprising the steps of:

emitting a beam of substantially non-visible electromagnetic radiation having a predetermined wavelength range towards the object;

scanning the beam of electromagnetic radiation in a direction that has at least a component transverse to the predetermined direction;

sensing radiation in the predetermined wavelength range which is reflected in a specular manner by the object; and determining the presence and/or absence of a coating on the object on the basis of the magnitude of specularly reflected radiation.

19. A method according to claim 18 and including the step of chopping the emitted signal to facilitate amplification of a narrow frequency band.

20. A method according to claim 19, wherein the chopping frequency is more than 50 kHz.

21. A method according to claim 18 and including the step of chopping the detected signal to facilitate amplification of a narrow frequency band.

22. A method according to claim 21, wherein the chopping frequency is more than 50 kHz.

23. A method according to claim 18, wherein the scanning is effected electronically.

24. A method according to claim 23, wherein the electronic scanner comprises at least one of an emitter and a sensor in the form of a linear array.

25. A method according to claim 24, wherein the linear array comprises a linear CCD device.

26. A method according to claim 23, wherein the electronic scanner comprises a plurality of emitters which emit radiation which falls on different regions of the object.

27. A method according to claim 26, wherein the emitters are operated sequentially.

28. A method according to claim 18, wherein the beam of radiation is scanned back and forth.

29. A method according to claim 18, wherein the transverse component is substantially perpendicular to the predetermined direction.

30. A method according to claim 18 and including the step of focussing specularly reflected radiation onto the sensor.

31. A method according to claim 18, wherein the presence and/or absence of a coating on the object is determined by signal processing means adapted to process signals generated by the sensor in response to any specularly reflected radiation.

32. A method according to claim 31, wherein the signal processing means incorporates reference data with which it compares a received signal sequence from the sensor to determine if there is a fault in the coating or not.

33. A method according to claim 32, wherein the reference data is automatically updated by the signal processing means.

* * * * *